United States Patent [19]

Broussalian

[11] 3,980,765

[45] Sept. 14, 1976

[54] HALOGENATED IMMUNOADSORBENT

[76] Inventor: George L. Broussalian, 233 S. Brookhurst, Anaheim, Calif. 92804

[22] Filed: Oct. 1, 1973

[21] Appl. No.: 402,179

[52] U.S. Cl. ............................ 424/1; 252/408; 252/429 A; 424/12
[51] Int. Cl.² ............... A61K 43/00; A61K 39/00; G01N 31/08; G01N 33/16
[58] Field of Search ......... 252/301.1 R, 410, 429 R, 252/429 A, 441, 408; 424/1, 12, 177

[56] References Cited
UNITED STATES PATENTS

| | | | |
|---|---|---|---|
| 3,410,839 | 11/1968 | DeCarvalho | 424/12 X |
| 3,553,310 | 1/1971 | Csizmas et al. | 424/12 X |

OTHER PUBLICATIONS

Colt et al., "A sensitive New Immunoassay for Calcitonin Employing Labeled Antibody," in Journal of Clinical Endocrinology and Metabolism, vol. 32, Feb. 1971, pp. 285–287.

Arrameas et al., "Biologically Active Water Insoluble Polymers," in Journal of Biological Chemistry, vol. 242, No. 7, Apr. 10, 1967, pp. 1651–1659.

Primary Examiner—Benjamin R. Padgett
Assistant Examiner—Christine M. Nucker
Attorney, Agent, or Firm—Bruce A. Jagger

[57] ABSTRACT

An immunoadsorbent in which the specific immunologically reactive protein is polymerized with a halogenated proteinaceous material. The halogenated immunoadsorbent is a fine granular, filterable material having generally stable characteristics.

19 Claims, No Drawings

HALOGENATED IMMUNOADSORBENT

Immunoadsorbents are immunologically reactive substances which have either antigen or antibody properties. The adsorptive properties of immunoadsorbents are attributable to the highly specific and sensitive reaction between antigens and antibodies. This highly specific and sensitive reaction is peculiar to biological systems. Antigens and antibodies are both protein materials. A living biological system has the remarkable property of being able to manufacture an antibody which exactly matches a foreign antigen. Thus, the fact that a specific antigen or antibody will react only with its exact counterpart permits the use of immunoadsorbents as analytical reagents in detecting and measuring minute quantities of protein mattter; such as, hormones, peptides, viruses, and vitamins, in biological fluids. Immunoadsorbents have, for example, been used for the quantitative determination of hormones in body fluids. Immunoadsorbents have also been used in the isolation, through adsorption and subsequent recovery, of antigens and antibodies. Immunoadsorbents have also been used in the differential diagnosis of allergies; the detection of infectious disease, such as hepatitis; and in the detection of drugs in body fluids.

The utilization of immunoadsorbent in test procedures requires the use of a tracer or labeling material. Suitable labeling materials include, for example, radioactive compounds as well as other readily detectable materials. Radioactive elements are generally favored for use as tracers or labeling compounds because of their ease of detection. When radioactive elements, such as iodine, are used, the test method is referred to as radioimmunoassay.

A typical radioimmunoassay procedure is used to measure the level of insulin hormone in human serum. In performing the test a small predetermined amount of antibody in the form of a halogenated immunoadsorbent of this invention is allowed to react with a slight excess of insulin which has been labeled or tagged with radioactive iodine, a gamma emitter. After the reaction is complete, the antibody is separated by filtration, and the precipitate is washed so as to separate the excess tagged insulin from the precipitate. The radioactivity in the washed precipitate is counted so as to establish a standard for the immunoadsorbent antibody when the antibody is completely saturated with radioactive tagged insulin antigen. The predetermined standard quantity of the patient's serum is admixed with a standard quantity of the radioactively tagged insulin. This admixture is in turn admixed with a known standard quantity of the immunoadsorbent antibody. The untagged insulin from the patient's serum competes with the tagged insulin for adsorption on the immunoadsorbent antibody. The tagged insulin is identical in its reactive characteristics with the antibody to the untagged insulin from the patient's serum. The competition for reactive sites on the immunoadsorbent antibody between the tagged and the untagged insulin will give a concentration of radioactive material in the fully reacted immunoadsorbent which is exactly proportional to the original quantities of the untagged insulin in the patient's serum. The resultant solid immunoadsorbent precipitate is washed and filtered using good techniques so as to separate the unreacted insulin and the radioactivity is then counted. From a comparison of the radioactive count obtained for the immunoadsorbent which is completely saturated with tagged antigen with the radioactive count obtained when the tagged and untagged insulin have competed for the antibody in the immunoadsorbent, it is possible to determine very precisely the quantity of insulin in the patient's serum.

Immunoassay procedures have wide applicability to the solution to many difficult analytical and isolation problems.

Difficulties had previously been experienced in immunoassay work in that the immunoadsorbents had generally been of such a nature that they formed colloids or slimy precipitates which are difficult to separate and filter or decant from aqueous mediums. Also, the resultant products had generally been somewhat unstable. Very critical and sensitive procedures had been required for the tagging of antibodies, in particular, with radioactive iodine. Previous methods of preparation of immunoadsorbents were often difficult and tedious to carry out, and the antigen or antibody was often damaged during preparation so that the resultant immunoadsorbent exhibited a low level of immune response activity. In use, previous immunoadsorbents sometimes yielded somewhat inaccurate results because the immunoadsorbent exhibited some nonspecific adsorption toward the specific material being tested for due to the fact that material was adsorbed by the immunoadsorbent at sites other than the specific antigen or antibody for which the immunoadsorbent was designed.

According to the present invention, these and other disadvantages in the prior art have been overcome.

According to the present invention, a halogenated proteinaceous material is polymerized with a specific immunologically reactive protein to provide a halogenated immunoadsorbent. The resultant halogenated immunoadsorbent is a high molecular weight material which is granular and filterable. The product stability is enhanced by its insolubility and large particle size. In use this immunoadsorbent exhibits very little nonspecific adsorption because the steric interference by the halogen atoms in the proteinaceous material minimizes the nonspecific adsorption of the antigen or antibody which is being tested for by portions of the immunoadsorbent other than the specific immunologically reactive protein which was polymerized with the halogenated proteinaceous material.

The halogenated immunoadsorbents which are substantially saturated with halogen, as determined by titration, are useful in the preparation of tagged or labeled antibodies or antigens, particularly antibodies which have been labeled with radioactive iodine (I-125 or I-131).

The proteinaceous material which is the immunologically inert backbone for the halogenated immunoadsorbent may be selected from a wide variety of natural and synthetic proteinaceous materials. This proteinaceous material may be from animal or plant sources, including, for example, casein, egg albumin and globulin, linseed meal, peanut flour, soybean protein, wheat gluten, coconut meal, and the like. The proteinaceous material may be pure or mixed, as desired.

The preferred halogen is iodine; however, bromine and chlorine and mixtures of halogens may be used if desired.

Several methods are known for halogenating proteinaceous materials. The halogenation procedures used according to the present invention are those in which the protein is halogenated with a minimum of damage to the proteinaceous material itself. It is desired to avoid denaturing the protein during the halogenation process.

Iodinating procedures which are suitable for producing iodinated proteinaceous material according to the present invention include the following procedures:

Pulverized iodine may be added slowly with continuous stirring to an aqueous admixture of proteinaceous material. The pH of the aqueous admixture is maintained at a value of from about 6.8 to 10.0 with the preferred pH range being from about 7.5 to 9. The temperature of the admixture is held at a value of from about 15° to 40° centigrade with a temperature of from about 30 to 40° centigrade being preferred. Sodium bicarbonate or a dilute solution of sodium hydroxide is added to maintain the reaction within the desired pH range. When it is desired to substantially saturate the proteinaceous material with iodine, the pH is maintained in the range of from about 8 to 10. Instead of crystalline iodine, a solution of iodine, such as Lugol's solution, may be used. Lugol's solution is an aqueous admixture containing 5 percent dissolved iodine and potassium iodide. The potassium iodide permits the solubilization of the crystalline iodine in the aqueous admixture. The reaction is allowed to proceed to completion. The time required to complete the reaction depends upon the reaction temperature with the higher temperatures requiring shorter reaction times. At a temperature of about 35° centigrade, the reaction is generally considered to be complete in about 2 hours.

Where it is desired to substantially saturate the proteinaceous material with iodine, the iodination is carried out and the point of substantial saturation is determined by titration. The protein material is subjected to iodination under conditions which are believed to be sufficient to substantially saturate the proteinaceous material with iodine, and the reaction is allowed to proceed to completion. The resultant material is subjected to titration according to a procedure in which 10 millimols of a standard iodine solution is added to the aqueous admixture which contains the iodinated proteinaceous material, and the admixture is allowed to stand for a period of about 15 minutes at a pH of approximately 8 and a temperature of about 30° centigrade. The resultant admixture is back titrated with a standard solution of sodium thiosulfate. If none of the additional iodine has been consumed by reaction with the proteinaceous material, the proteinaceous material is assumed to be substantially saturated with iodine.

In general it has been found that the minimum amount of iodine required in the proteinaceous material before polymerization is approximately 200 parts by weight of iodine per 10,000 parts by weight of proteinaceous material. The minimum amount of bromine required in the proteinaceous material before polymerization is approximately 140 parts by weight of bromine per 10,000 parts by weight of proteinaceous material; and the minimum amount of chlorine is about 150 parts by weight of chlorine per 10,000 parts by weight of proteinaceous material. In general, the proteinaceous material should contain at least approximately 2 weight percent of halogen in the halogenated proteinaceous material. The proteinaceous material used should have an average molecular weight of at least about 5,000 so as to provide a sufficient number of halogen receptive sites.

The preferred procedure for brominating proteinaceous material includes the use of a water soluble bromide salt, such as potassium bromide, together with an oxidizing agent, such as potassium permanganate or sodium N-chloro-para-toluene sulfonamide (commonly known as Chloramine T), in an aqueous admixture with the proteinaceous material. The pH is maintained at a value of from approximately 6.8 to 10, and the temperature is maintained at from about 15° centigrade to 40° centigrade. The reaction is allowed to proceed for a period of from about 2 to 8 hours.

A preferred procedure for the chlorination of proteinaceous material includes the use of a basic solution of chlorine in water, for example, sodium hypochlorite. The pH of the aqueous admixture is maintained at a value of from about 6.8 to 10, and the temperature is maintained in the range of from about 15° centigrade to 30° centigrade. The chlorination reaction is allowed to proceed for from approximately 2 to 8 hours.

The halogenated proteinaceous material is polymerized with the specific preselected antigen or antibody in an aqueous admixture. The halogenated proteinaceous material is admixed with the specific immunologically reactive protein in the desired ratio which generally ranges from about 1 to 100 parts by weight of halogenated proteinaceous material to 1 part by weight of the specific immunologically reactive protein. In general, the proportions range from about 1 part specific immunologically reactive protein to from about 4 to 10 parts by weight of halogenated proteinaceous material.

Polymerization is generally accomplished in an aqueous admixture containing the desired predetermined proportions of halogenated proteinaceous material and specific immunologically reactive protein. The pH of the mixture of proteinaceous materials is adjusted to approximately 5 to 7. A polymerizing agent, such as chloroformic acid ester or a dialdehyde, is added with gentle stirring. A small amount of the polymerization agent is utilized. The polymerization is carried out at a temperature of from about 15° to 40° centigrade. The reaction admixture is allowed to stand for a few hours, and the precipitate which is formed is separated by filtration. The precipitate is a fine granular material which is readily filtered or decanted. In decantation the admixture is centrifuged, and the liquid phase is decanted from the precipitate which is in a layer at the bottom of the vessel.

One convenient polymerization agent is ethyl chloroformate, although short chain alkyl esters, such as isobutyl chloroformate may also be used. Glutaraldehyde is also a convenient polymerization agent, but other materials, such as succinaldehyde or even aromatic dialdehydes, may be used if desired. Another suitable polymerization agent or catalyst is S-acetyl-mercaptosuccinic anhydride.

The physical properties of the immunoadsorbent vary with the pH of the polymerization reaction and the degree of halogenation. The reaction produces an immunoadsorbent with the desired filterable and decantable characteristics at a pH of from about 5 to 7. Below or above this pH range the polymer rapidly becomes colloidal, particularly at high degrees of halogen saturation.

The proportion of antigen or antibody to halogenated proteinaceous material is dependent upon the strength or titer of the antigen or antibody. As the titer of the immunologically reactive protein increases, the proportion of this reactive material in the polymerization admixture decreases. In general the titer of the antigen or antibody is such that the proportion of immunologically reactive protein to halogenated proteinaceous material is less than about 1 to 100. The usual titer values are such as to require ratios from approximately 1 to 4 to 1 to 10, with some materials ranging as low as about 1 to 1 and as high as about 1 to 20.

The procedures for preparing the immunoadsorbents according to the present invention involve straightforward, easy to perform steps which do substantially no damage to the antigen or antibody. The resultant immunoadsorbent product is finely granular and filterable because of its high molecular weight and has a low nonspecific adsorption, due mainly to steric interference by the halogen atoms, and in particular iodine; and the immunoadsorbent product is stable partly because of its insolubility and large particle size. When the product is substantially saturated with halogen, it is suitable for use in tagging sensitive antibodies or antigens.

In preparing an immunoadsorbent which is to be used in the labeling of sensitive antibodies or antigens with detectable materials, such as radioactive iodine, the halogenated proteinaceous material is saturated with halogen. Excess halogen is used during the halogenation reaction, and the material is tested by titration, as indicated above, to determine that substantial saturation has been achieved. Because of the extremely complex nature of most high molecular weight protein materials, it is not possible to precisely identify when saturation with halogen has been achieved. The term "substantial saturation" or "substantially saturated" as used herein means that the protein does not accept any more halogen under halogenating conditions, as indicated above. The absence of further reaction by halogen with the proteinaceous material is determined by titration procedures, as indicated above.

In the preparation of an immunoadsorbent which is to be used in labeling sensitive immunologically reactive proteins, particularly antibodies, the proteinaceous material is substantially saturated with halogen before being polymerized with the specific antigen or antibody. The polymerization reaction is completed, and the fine granular precipitate is recovered, filtered, and washed.

The antibody or antigen which is to be labeled is contacted with the resultant, substantially saturated halogenated immunoadsorbent. The antibody or antigen is adsorbed by the immunoadsorbent. The precipitate is again filtered and washed and is then contacted with the desired labeling material in an aqueous admixture. When the labeling material is radioactive iodine, the halogenated immunoadsorbent with the adsorbed immunologically reactive material is contacted with a dilute solution of Chloramine T and sodium iodide in which the iodine is radioactive. The pH is maintained at about 7 to 8.5. The radioactive iodine reacts with the only reactive sites available in the combined immunoadsorbent, which reactive sites are found in the second immunologically reactive protein. The substantial saturation of the proteinaceous material with halogen prevents the radioactive iodine from reacting with this material. In general, the reactive sites on the first immunologically reactive protein do not consume any appreciable amount of the radioactive iodine. Some reactive sites are usually available on the first immunologically reactive protein; however, most of the radioactive iodine is combined with the second immunologically reactive protein. After the iodination reaction has been permitted to proceed for a period of from about 1 to 10 minutes, the second immunologically reactive protein is stripped from the immunoadsorbent by acidifying the solution and then rapidly neutralizing it. The acidification accomplishes the stripping of the adsorbed second immunologically reactive protein from the immunoadsorbent, and the rapid neutralization prevents the destruction of the second immunlogically reactive protein which is now tagged with radioactive iodine. The tagged protein remains in solution while the immunoadsorbent remains as a fine precipitate which is easily separated from the aqueous solution by filtration or decantation.

The procedure for tagging immunologically reactive proteins is applicable to both antigens and antibodies, and it is particularly applicable to antibodies which tend to be more sensitive and more easily damaged than are the antigens.

If the immunoadsorbent is to be used in the preparation of tagged antigens, it is necessary to substantially saturate the proteinaceous material with halogen so that an excessive amount of radioactive iodine will not be consumed during the tagging process. If it is not desired to use the immunoadsorbent in the labeling of immunologically reactive proteins, then the halogenated proteinaceous material need be only partially saturated to produce the desired characteristics of fine granular texture, low blank and nonspecific adsorption and stability. In general, the immunadsorbent should contain at least about 0.008 mole of halogen per 100 grams of immunoadsorbent. Preferably, the immunoadsorbent should contain at least about 0.025 mole of halogen per 100 grams of immunoadsorbent. In general, for chlorinated immunoadsorbents at least about 0.025 mole of chlorine should be present in each 100 grams of immunoadsorbent.

The following examples are provided to illustrate and not to limit the invention. All parts and percentages herein are by weight unless otherwise indicated.

EXAMPLE I

A halogenated proteinaceous material is prepared according to the following procedure.

A 2 gram quantity of human globulin is admixed with 100 milliliters distilled water at a temperature of about 37° centigrade. The distilled water contains about 3.0 grams of sodium bicarbonate. The pH of the aqueous admixture is maintained at a value of about 8.5. The globulin material has an average molecular weight of about 100,000. About 10 milliliters of Lugol's solution (5 percent iodine) is added dropwise with constant stirring to the aqueous admixture while the pH is maintained at a value of about 8.5, and the temperature is maintained at about 37° centigrade. The reactive admixture is allowed to stand for about 3 hours after the addition of the Lugol's solution is complete. The reaction product is then isolated by acidifying the mixture to a pH of about 5 with dilute hydrochloric acid and then filtering. The isolated reaction product is redissolved in 100 milliliters of 0.1 percent sodium hydroxide solution to give an iodinated globulin in solution. The purified iodinated globulin contains about 12 weight percent of iodine.

This example is repeated utilizing potassium bromide and Chloramine T in place of the Lugol's solution. About 100 milliliters of potassium bromide-Chloramine T solution is used. This potassium bromide-Chloramine T solution contains about 0.5 gram of potassium bromide and about 1.0 gram of Chloramine T. The resultant product is a brominated globulin in solution, which is precipitated with acid and redissolved with base, as above in this example, for purification purposes. The purified brominated globulin contains about 16 weight percent of bromine.

This example is repeated using 100 milliliters of a 3 percent basic solution of sodium hypochlorite which is admixed and reacted according to the procedure of this example. The resultant product is a chlorinated globulin in solution, which is precipitated and redissolved as above in this example. The purified chlorinated globulin contains about 7 weight percent of chlorine.

EXAMPLE II

Halogenated human globulin is polymerized with an immunologically reactive protein, specifically an antigen, which has a specific predetermined immune response.

A 20 milliliter quantity of the aqueous solution of the iodinated human globulin prepared in Example I, above, is admixed with a 5 milligram quantity of porcine insulin. The pH of the resultant admixture is adjusted to about 6 with dilute hydrochloric acid. A 0.5 milliliter quantity of ethyl chloroformate is added dropwise with stirring to the admixture, and the admixture is then set aside and allowed to stand for 3 hours at about 25° centigrade. At the conclusion of this period of time, the pH of the admixture is adjusted to about 7 with dilute sodium hydroxide solution. A precipitate forms which is collected on a Whatman No. 1 filter paper, under suction, and is washed successively with 100 milliliters of normal saline solution, 0.1 percent sodium carbonate solution, and distilled water. The precipitate is dried in a desiccator and pulverized to a fine granular product by means of a mortar and pestle. The granular product contains about 1,200 parts by weight of iodine per 10,000 parts by weight of the product.

The activity of the iodinated immunoadsorbent prepared in this example is tested. The fine granular iodinated immunoadsorbent is suspended in 100 milliliters of 0.1 molar phosphate buffer solution (pH 7.4) containing 0.1 percent albumin. A 0.1 milliliter quantity of the resultant slurry is admixed with one milliliter of normal saline solution and 0.1 milliliter of I-125 labeled insulin antibody equivalent to 2 nanograms insulin. After a period of 1 hour at 35° centigrade, the slurry is filtered on a Whatman No. 1 filter paper. About 50 percent of the I-125 activity is bound to the precipitate. Repeating this experiment using an equivalent amount of I-125 labeled insulin results in less than 1 percent of the I-125 activity being bound to the precipitate indicating a low blank or nonspecific adsorption.

When the fine granular product is stored either in the form of a buffered slurry or as a dried powder in a refrigerator at 0° to 8° centigrade for a period of 6 months, the immunoadsorbent shows an insignificant lowering of immunological activity.

For purposes of comparison, an immunoadsorbent is prepared as described in this example, except that it is prepared from human globulin which has not been halogenated. This unhalogenated immunoadsorbent shows a loss of about 7 percent in activity after only 2 months storage and exhibits a blank of about 5 percent. It is not possible to collect this unhalogenated immunoadsorbent on a Whatman No. 1 filter paper because it passes through the paper. This unhalogenated immunoadsorbent is a very fine colloidal material.

The procedures of this example are repeated to produce an iodinated immunoadsorbent which has antibody activity. A 20 milliliter quantity of aqueous iodinated globulin solution prepared in Example I and a 1.0 milliliter quantity of rabbit human growth hormone antiserum are admixed and allowed to react under the conditions described above in this example. The physical characteristics of the resultant precipitate are substantially identical to those described above in that it is a fine granular, easily filtered material. When the activity of the antibody immunoadsorbent is tested by admixing a 0.1 milliliter quantity of buffered slurry with 1 milliliter of normal saline solution and 0.1 milliliter of I-125 labeled human growth hormone equivalent to 2 nanograms, according to the procedure described above in this example, it is found that about 30 percent of I-125 activity is bound to the precipitate. When an equivalent amount of I-125 labeled insulin or other labeled protein is employed in place of the specific antigen which corresponds to this antibody immunoadsorbent, the I-125 activity bound to the precipitate is only about 1 percent, indicating a low blank or nonspecific adsorption. Storage of either the buffered slurry or the dried granular precipitate in a refrigerator at 0° to 8° centigrade for a period of 6 months does not significantly decrease the activity of the iodinated antibody immunoadsorbent. The iodinated antibody immunoadsorbent contains about 1,000 parts by weight of iodine per 10,000 parts of iodinated antibody immunoadsorbent.

This example is repeated utilizing a 20 milliliter portion of the brominated human globulin prepared in Example I, above, in place of the iodinated globulin. The physical characteristics of the resultant precipitate are substantially identical to those of the iodinated immunoadsorbent in that it is a fine granular material which is readily separated by filtration or decantation from the liquid phase. The activity of the brominated antibody immunoadsorbent is determined, as described hereinabove, using I-125. About 30 percent of the I-125 activity is bound to the antibody immunoadsorbent when I-125 labeled antigen is used. The blank or nonspecific adsorption is about 1 percent, according to the same procedures described above, using an immunologically reactive I-125 labeled material other than the specific antigen to which the brominated antibody immunoadsorbent is tailored. The stability of the brominated antibody immunoadsorbent is such that in either the slurry or dried granular form the immunological activity begins to deteriorate significantly when stored under refrigeration at 0 to 8 degrees centigrade for about 4 months.

This example is repeated using a 20 milliliter portion of the chlorinated human globulin produced in Example I, above utilizing the procedures of this example. The physical characteristics of this resultant chlorinated antibody immunoadsorbent are substantially identical to those of the iodinated and brominated immunoadsorbents in that the precipitates are fine granular materials which are easily filtered or decanted to separate them from the aqueous phase. The activity of the chlorinated antibody immunoadsorbent is about 20 percent as determined through the use of I-125 labeled antigen, and the blank or nonspecific adsorption is determined to be about 3 percent using an I-125 labeled antigen which is not specific to the chlorinated antibody immunoadsorbent. The chlorinated antibody immunoadsorbent tends to lose a significant amount of its immunological activity when it is stored under refrigeration at 0° to 8° centigrade for longer than about 2 months.

When the procedures of Examples I and II, hereinabove, are repeated utilizing varying quantities of iodine, bromine, and chlorine respectively, it is determined that immunoadsorbents in which the immunoadsorbent contains less than about 0.008 mole of halogen per 100 grams of immunoadsorbent do not possess the physical characteristics of being easily filtered or decanted from contact with the liquid phase. The full advantages of stability, low blank and ease of separation, are generally not achieved with immunoadsorbents which contain less than about 0.025 mole of halogen per each 100 grams of immunoadsorbent. When chlorine is utilized as the halogen, the moles of chlorine should be at least doubled and preferably tripled over what would be required if iodine were being used as the halogen in the same immunoadsorbent.

The filtrability or decantability of the immunoadsorbents is conveniently determined by placing them in distilled water, pH 7, at a temperature of about 25° centigrade. The halogenated immunoadsorbents which enjoy the advantages of the present invention as regards filtrability are those which are readily filterable under these conditions on a Whatman No. 1 filter paper. The pH of the polymerization reaction admixture should be maintained between about 5 and 8. At a pH in excess of about 8 the halogenated immunoadsorbent becomes colloidal so that it is no longer readily filterable. Also a pH of below about 4 the halogenated immunoadsorbent is not readily filterable from the aqueous phase.

Some of the advantages of the present invention are achieved by polymerizing the halogenated proteinaceous material produced in Example I with itself and using this fine granular precipitate as a filtering aid for a near colloidal immunoadsorbent. The fine granular precipitate formed by the polymerized halogenated proteinaceous material is admixed with a near colloidal suspension of nonhalogenated immunoadsorbent. The solid phase material is separable either by filtration or decantation from the liquid phase, and the resultant product is a physical admixture of polymerized halogenated proteinaceous material and immunoadsorbent. Some of the immunoadsorbent is lost in the filtration, but a good portion of the immunoadsorbent is retained on the surface of the polymerized halogenated proteinaceous material. This physical admixture exhibits a low blank and nonspecific adsorbent characteristic. Apparently the halogen in the polymerized halogenated proteinaceous material does not enter into the adsorption process. This physical admixture is useful where it is considered undesirable to directly halogenate the proteinaceous material portion of the immunoadsorbent. The nonhalogenated materials which are described herein as "colloidal" or "near colloidal" are fine suspended materials that are not true colloids but which are not filterable on Whatman No. 1 filter paper or cannot be readily centrifuged and decanted with conventional laboratory techniques.

EXAMPLE III

Example I, hereinabove, is repeated except that an excess amount of iodine is provided so as to produce a substantially saturated iodinated globulin.

Example I is repeated except that a 20 milliliter quantity of Lugol's solution is employed. The resultant substantially saturated iodinated globulin is subjected to a titration test to determine whether it is substantially saturated as follows:

A 10 milliliter quantity of the resultant substantially saturated iodinated globulin is admixed with a 50 milliliter quantity of 0.1N standard iodine solution. The mixture is allowed to stand for 15 minutes at a temperature of 30° centigrade. The pH of the liquid admixture is maintained throughout this 15 minute period at a pH of between about 8 and 10. The liquid admixture is then titrated with an 0.1N solution of sodium thiosulfate in water using starch solution as the indicator. The following results obtained in this back titration indicate that none of the iodine in the standard solution reacted with the iodinated globulin, thus indicating that the globulin is substantially saturated with iodine. The volume of standard sodium thiosulfate solution required for the back titration is about 49 milliliters, indicating that the globulin is better than 98 percent saturated with iodine.

A 0.4 gram quantity of the substantially iodine saturated globulin produced in this example is polymerized as in Example II, hereinabove, with rabbit human growth hormone antiserum and the resultant antibody iodinated immunoadsorbent is admixed with a 20 milliliter quantity of an aqueous solution containing about 0.1 milligram of crystalline human growth hormone. The temperature of the admixture is maintained at about 37° centigrade, and it is allowed to stand with gentle stirring for a period of about 6 hours. The resultant combined immunoadsorbent is recovered by filtration and repeated washing on a Whatman No. 1 filter.

A 0.4 gram sample of the combined immunoadsorbent is admixed with 5 milliliter of a phosphate buffered, pH 7.4, solution of sodium iodide in which the iodine is a radioactive isotope, I-125, of about 5 millicurie activity. To this admixture is added a solution of 1 milligram Chloramine T in 0.2 milliliter water. This admixture is allowed to react for 2 minutes at about 25° centigrade, and the reaction is terminated by adding 2 milligrams of sodium bisulfite in 0.2 milliliter of water. The precipitate is filtered on a Whatman No. 1 filter paper and washed. The filtered and washed precipitate is suspended in water which is acidified carefully as rapidly as possible with a dilute solution of hydrochloric acid to a pH of about 2. The acidified solution is carefully neutralized as promptly as possible with dilute sodium hydroxide solution to a pH of about 7. The fine granular precipitate is filtered from the solution. The solution contains about 0.1 milligram of antigen, human growth hormone, which has been tagged with radioactive iodine to the extent of about 50 microcuries per microgram of the antigen. The recovered antibody polymer is essentially unaltered and may be used again in a repetition of this example.

What is claimed is:

1. A halogenated immunoadsorbent comprising: a halogenated proteinaceous material polymerized with an immunologically reactive protein, which immunologically reactive protein has a specific immune response, said halogenated proteinaceous material containing an amount of halogen sufficient to cause said halogenated immunoadsorbent to be a readily filterable, fine granular precipitate in water at a pH of about 7 and a temperature of about 25 degrees centigrade.

2. A halogenated immunoadsorbent of claim 1 wherein the halogen is bromine.

3. A halogenated immunoadsorbent of claim 1 wherein the halogen is iodine.

4. A halogenated immunoadsorbent of claim 1 wherein said halogenated proteinaceous material is substantially saturated with halogen as determined by titration in an aqueous admixture at a pH of about 8 and a temperature of about 30° centigrade.

5. A halogenated immunoadsorbent of claim 1, wherein a second immunologically reactive protein is immunologically adsorbed on the immunologically reactive protein, said halogenated proteinaceous material is substantially saturated with halogen as determined by titration in an aqueous admixture at a pH of about 8 and a temperature of about 30° centigrade.

6. A halogenated immunoadsorbent of claim 5, wherein the second immunologically reactive protein is combined with a detectable amount of a labeling material.

7. A halogenated immunoadsorbent of claim 1 wherein the halogen is a mixture of halogens.

8. An iodinated immunoadsorbent comprising: an iodinated proteinaceous material polymerized with an immunologically reactive protein, which immunologically reactive protein has a specific immune response, said iodinated proteinaceous material containing an amount of iodine sufficient to cause said iodinated immunoadsorbent to be a readily filterable, fine granular precipitate in water at a pH of about 7 and a temperature of about 25° centigrade.

9. An iodinated immunoadsorbent of claim 8 wherein said proteinaceous material is substantially saturated with iodine as determined by titration in an aqueous admixture at a pH of about 8 and a temperature of about 30° centigrade.

10. A brominated immunoadsorbent comprising: a brominated proteinaceous material polymerized with an immunologically reactive protein, which immunologically reactive protein has a specific immune response, said brominated proteinaceous material containing an amount of bromine sufficient to cause said brominated immunoadsorbent to be a readily filterable, fine granular precipitate in water at a pH of about 7 and a temperature of about 25° centigrade.

11. An iodinated immunoadsorbent comprising: an iodinated proteinaceous material polymerized with an immunologically reactive protein, which immunologically reactive protein has a specific immune response, said iodinated immunoadsorbent containing at least about 0.008 mole of iodine and up to an amount of iodine sufficient to substantially saturate said iodinated proteinaceous material for each 100 grams of iodinated immunoadsorbent.

12. A brominated immunoadsorbent comprising: a brominated proteinaceous material polymerized with an immunologically reactive protein, which immunologically reactive protein has a specific immune response, said brominated immunoadsorbent containing at least about 0.008 mole of bromine and up to an amount of bromine sufficient to substantially saturate said brominated proteinaceous material for each 100 grams of brominated immunoadsorbent.

13. A chlorinated immunoadsorbent comprising: a chlorinated proteinaceous material polymerized with an immunologically reactive protein, which immunologically reactive protein has a specific immune response, said chlorinated immunoadsorbent containing at least about 0.025 mole of chlorine and up to an amount of chlorine sufficient to substantially saturate said chlorinated proteinaceous material for each 100 grams of chlorinated immunoadsorbent.

14. A process comprising:
   halogenating a proteinaceous material in an aqueous admixture at a pH of from about 6.8 to 10 and a temperature of from about 15° centigrade to 40° centigrade to produce halogenated proteinaceous material;
   polymerizing said halogenated proteinaceous material with an immunologically reactive protein, which immunologically reactive protein has a specific predetermined immune reaction, to produce a halogenated immunoadsorbent.

15. A process of claim 14 including halogenating the proteinaceous material with an amount of iodine sufficient to produce a halogenated immunoadsorbent in which the iodine is present in an amount of at least about 0.008 mole per 100 grams of said halogenated immunoadsorbent and up to an amount where said halogenated proteinaceous material is substantially saturated with iodine.

16. An iodinated immunoadsorbent of claim 8 wherein a second immunologically reactive protein is immunologically adsorbed on the immunologically reactive protein, said iodinated proteinaceous material is substantially saturated with iodine as determined by titration in an aqueous admixture at a pH of about 8 and a temperature of about 30° centigrade.

17. An iodinated immunoadsorbent of claim 16, wherein the second immmunologically reactive protein is combined with a detectable amount of labeling material.

18. An iodinated immunoadsorbent of claim 17 wherein the labeling material is radioactive iodine.

19. A physical admixture comprising:
   polymerized halogenated proteinaceous material and an immunoadsorbent, said immunoadsorbent consisting essentially of a protein material polymerized with an immunologically reactive protein which immunologically reactive protein has a specific immune response, said polymerized halogenated proteinaceous material being formed by polymerizing halogenated proteinaceous material and containing an amount of halogen sufficient to cause said polymerized halogenated proteinaceous material to be a fine granular precipitate in water at a pH of about 7 and a temperature of about 25° centigrade, said immunoadsorbent being a near colloidal suspension in water at a pH of about 7 and a temperature of about 25° centigrade.

* * * * *